United States Patent [19]

Schlaeppi

[11] Patent Number: 5,296,352

[45] Date of Patent: Mar. 22, 1994

[54] MONOCLONAL ANTIBODIES DIRECTED AGAINST COMPLEXES FORMED BY THROMBIN AND HIRUDIN

[75] Inventor: Jean-Marc Schlaeppi, Basel, Switzerland

[73] Assignee: Ciba-Geigy Corporation, Ardsley, N.Y.

[21] Appl. No.: 763,860

[22] Filed: Sep. 23, 1991

[51] Int. Cl.$^5$ .................... A61K 35/14; C07K 15/00
[52] U.S. Cl. ................... 435/7.4; 435/70.21; 435/240.27; 435/7.9; 530/388.85; 530/389.3
[58] Field of Search ............ 530/388.85, 389.3; 435/70.21, 240.27, 7.9, 7.4

[56] References Cited

FOREIGN PATENT DOCUMENTS 0168342 1/1986 European Pat. Off. .
0380443 8/1990 European Pat. Off. .
0391433 10/1990 European Pat. Off. .

OTHER PUBLICATIONS

Dawes et al–Chem. Abst. vol. 102 (1985) p. 76950e.
Chuang et al–Chem. Abst. vol. 104 (1986) p. 10,448g.
Spinner et al–J. of Immunol. Methods–vol. 87 (1986) pp. 79–83.
Suzuku et al., *J. of Biol. Chem.*, 265:13263–13267 (1990).
Schlaeppi et al., *Eur. J. Biochem.*, 188:463–470 (1990).

*Primary Examiner*—Sam Rosen
*Attorney, Agent, or Firm*—W. Murray Spruill

[57] ABSTRACT

The invention concerns monoclonal antibodies which are directed against the thrombin/hirudin-complex and derivatives thereof, processes for their preparation, hybridoma cell lines secreting said monoclonal antibodies, and processes for the preparation of the hybridoma cell lines. Furthermore, the invention relates to the use of the monoclonal antibodies and/or their derivatives for the determination of the thrombin/hirudin-complex as well as to test kits comprising said monoclonal antibodies and/or their derivatives.

25 Claims, No Drawings

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
    ( A ) LENGTH: 65 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
    ( A ) ORGANISM: hirudo medicinalis
    ( C ) INDIVIDUAL ISOLATE: hirudin variant type HV1

( i x ) FEATURE:
    ( A ) NAME/KEY: Modified-site
    ( B ) LOCATION: 27
    ( D ) OTHER INFORMATION: /note="Lys may replaced by Ile or
      Glu"

( i x ) FEATURE:
    ( A ) NAME/KEY: Modified-site
    ( B ) LOCATION: 36
    ( D ) OTHER INFORMATION: /note="Lys may replaced by Ile or
      Glu"

( i x ) FEATURE:
    ( A ) NAME/KEY: Modified-site
    ( B ) LOCATION: 47
    ( D ) OTHER INFORMATION: /note="Lys may replaced by Ile or
      Glu"

( i x ) FEATURE:
    ( A ) NAME/KEY: Modified-site
    ( B ) LOCATION: 51
    ( D ) OTHER INFORMATION: /note="His may replaced by Leu or
      Asp"

( i x ) FEATURE:
    ( A ) NAME/KEY: Modified-site
    ( B ) LOCATION: 1..2
    ( D ) OTHER INFORMATION: /note="Val 1-Val 2 may be replaced
      by Thr or Leu-Thr"

( i x ) FEATURE:
    ( A ) NAME/KEY: Modified-site
    ( B ) LOCATION: 63
    ( D ) OTHER INFORMATION: /note="Tyr 63 is a modified Tyr
    ( R ) residue, wherein R is the phenolic
      hydroxygroup of Tyr (desulphatohirudin) or a
      O-SO3H group ( x i ) SEQUENCE DESCRIPTION: SEQ ID NO:1:

```
Val Val Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
            35                  40                  45

Gln Ser His Asn Asp Gly Asp Phe Glu Glu Ile Pro Glu Glu Tyr Leu
        50                  55                  60

Gln
65
```

( 2 ) INFORMATION FOR SEQ ID NO:2:

( i ) SEQUENCE CHARACTERISTICS:
    ( A ) LENGTH: 64 amino acids
    ( B ) TYPE: amino acid
    ( C ) STRANDEDNESS: single
    ( D ) TOPOLOGY: linear (ii) MOLECULE TYPE: peptide (iii) HYPOTHETICAL: NO (iv) ANTI-SENSE: NO (vi) ORIGINAL SOURCE:
  (A) ORGANISM: hirudo medicinalis
  (C) INDIVIDUAL ISOLATE: hirudin variant type HV1

(ix) FEATURE:
  (A) NAME/KEY: Modified-site
  (B) LOCATION: 27
  (D) OTHER INFORMATION: /note="Lys may replaced by Ile or Glu"

(ix) FEATURE:
  (A) NAME/KEY: Modified-site
  (B) LOCATION: 36
  (D) OTHER INFORMATION: /note="Lys may replaced by Ile or Glu"

(ix) FEATURE:
  (A) NAME/KEY: Modified-site
  (B) LOCATION: 47
  (D) OTHER INFORMATION: /note="Lys may replaced by Ile or Glu"

(ix) FEATURE:
  (A) NAME/KEY: Modified-site
  (B) LOCATION: 51
  (D) OTHER INFORMATION: /note="His may replaced by Leu or Asp"

(ix) FEATURE:
  (A) NAME/KEY: Modified-site
  (B) LOCATION: 1..2
  (D) OTHER INFORMATION: /note="Val 1-Val 2 may be replaced by Thr or Leu-Thr"

(ix) FEATURE:
  (A) NAME/KEY: Modified-site
  (B) LOCATION: 63
  (D) OTHER INFORMATION: /note="Tyr 63 is a modified Tyr (R) residue, wherein R is the phenolic hydroxygroup of Tyr (desulphatohirudin) or a O-SO3H group (xi) SEQUENCE DESCRIPTION: SEQ ID NO:2:

```
Val Val Tyr Thr Asp Cys Thr Glu Ser Gly Gln Asn Leu Cys Leu Cys
 1               5                   10                  15
Glu Gly Ser Asn Val Cys Gly Gln Gly Asn Lys Cys Ile Leu Gly Ser
                20                  25                  30
Asp Gly Glu Lys Asn Gln Cys Val Thr Gly Glu Gly Thr Pro Lys Pro
            35                  40                  45
Gln Ser His Asn Asp Gly Asp Phe Glu Glu Ile Pro Glu Glu Tyr Leu
        50                  55                  60
```

(2) INFORMATION FOR SEQ ID NO:3:

(i) SEQUENCE CHARACTERISTICS:
  (A) LENGTH: 63 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (vi) ORIGINAL SOURCE:
  (A) ORGANISM: hirudo medicinalis
  (C) INDIVIDUAL ISOLATE: hirudin variant type HV1

-continued ( i x ) FEATURE:
    ( A ) NAME/KEY: Modified-site
    ( B ) LOCATION: 27
    ( D ) OTHER INFORMATION: /note="Lys may replaced by Ile or
        Glu"

( i x ) FEATURE:
    ( A ) NAME/KEY: Modified-site
    ( B ) LOCATION: 36
    ( D ) OTHER INFORMATION: /note="Lys may replaced by Ile or
        Glu"

( i x ) FEATURE:
    ( A ) NAME/KEY: Modified-site
    ( B ) LOCATION: 47
    ( D ) OTHER INFORMATION: /note="Lys may replaced by Ile or
        Glu"

( i x ) FEATURE:
    ( A ) NAME/KEY: Modified-site
    ( B ) LOCATION: 51
    ( D ) OTHER INFORMATION: /note="His may replaced by Leu or
        Asp"

( i x ) FEATURE:
    ( A ) NAME/KEY: Modified-site
    ( B ) LOCATION: 1..2
    ( D ) OTHER INFORMATION: /note="Val 1-Val 2 may be replaced
        by Thr or Leu-Thr"

( i x ) FEATURE:
    ( A ) NAME/KEY: Modified-site
    ( B ) LOCATION: 63
    ( D ) OTHER INFORMATION: /note="Tyr 63 is a modified Tyr
    ( R ) residue, wherein R is the phenolic
        hydroxygroup of Tyr (desulphatohirudin) or a
        O-SO3H group ( x i ) SEQUENCE DESCRIPTION: SEQ ID NO:3:

```
Val Val Tyr Thr Asp Cys Thr Glu Ser Gly Gln Asn Leu Cys Leu Cys
 1               5                  10                      15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr
        50                  55                  60
```

( 2 ) INFORMATION FOR SEQ ID NO:4:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Hirudo medicinalis
        ( C ) INDIVIDUAL ISOLATE: hirudin variant type HV2

( i x ) FEATURE:
        ( A ) NAME/KEY: Modified-site
        ( B ) LOCATION: 1..2
        ( D ) OTHER INFORMATION: /note="Ile 1 may be replaced by
            Val and Thr 2 by Val"

( i x ) FEATURE:
        ( A ) NAME/KEY: Modified-site
        ( B ) LOCATION: 47
        ( D ) OTHER INFORMATION: /note="Asn may be replaced by Lys
            or Arg or His"

( i x ) FEATURE:
    ( A ) NAME/KEY: Modified-site
    ( B ) LOCATION: 63
    ( D ) OTHER INFORMATION: /note="Tyr 63 is a modified Tyr
    ( R ) residue, wherein R is the phenolic
        hydroxygroup of Tyr (desulphatohirudin) or a
        O-SO3-H group ( x i ) SEQUENCE DESCRIPTION: SEQ ID NO:4:

```
Ile Thr Tyr Thr Asp Cys Thr Glu Ser Gly Gln Asn Leu Cys Leu Cys
1               5                   10                  15

Glu Gly Ser Asn Val Cys Gly Lys Gly Asn Lys Cys Ile Leu Gly Ser
            20                  25                  30

Asn Gly Leu Gly Asn Gln Cys Val Thr Gly Glu Gly Thr Pro Asn Pro
        35                  40                  45

Glu Ser His Asn Asn Gly Asp Phe Glu Glu Ile Pro Glu Glu Tyr Leu
    50                  55                          60

Gln
65
```

( 2 ) INFORMATION FOR SEQ ID NO:5:

( i ) SEQUENCE CHARACTERISTICS:
        ( A ) LENGTH: 66 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: hirudo medicinalis
        ( C ) INDIVIDUAL ISOLATE: hirudin variant type PA (HV3)

( i x ) FEATURE:
        ( A ) NAME/KEY: Modified-site
        ( B ) LOCATION: 64
        ( D ) OTHER INFORMATION: /note="Tyr 64 is a modified Tyr
        ( R ) residue, wherein R is the phenolic
            hydroxygroup of Tyr (desulphatohirudin) or a
            O-SO3H group ( x i ) SEQUENCE DESCRIPTION: SEQ ID NO:5:

```
Ile Thr Tyr Thr Asp Cys Thr Glu Ser Gly Gln Asn Leu Cys Leu Cys
1               5                   10                  15

Glu Gly Ser Asn Val Cys Gly Lys Gly Asn Lys Cys Ile Leu Gly Ser
            20                  25                  30

Gln Gly Leu Asp Asn Gln Cys Val Thr Gly Glu Gly Thr Pro Leu Pro
        35                  40                  45

Gln Ser His Asn Gln Gly Asp Phe Glu Pro Ile Pro Glu Asp Ala Tyr
    50                  55                          60

Asp Glu
65
```

( 2 ) INFORMATION FOR SEQ ID NO:6:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide (iii) HYPOTHETICAL: NO (iv) ANTI-SENSE: NO (vi) ORIGINAL SOURCE:
  (A) ORGANISM: hirudo medicinalis
  (C) INDIVIDUAL ISOLATE: hirudin variant type PA (HV3)

(xi) SEQUENCE DESCRIPTION: SEQ ID NO:6:

```
Ile Thr Tyr Thr Asp Cys Thr Glu Ser Gly Gln Asn Leu Cys Leu Cys
 1               5                  10                  15

Glu Gly Ser Asn Val Cys Gly Lys Gly Asn Lys Cys Ile Leu Gly Ser
            20                  25                  30

Gln Gly Leu Asp Asn Gln Cys Val Thr Gly Glu Gly Thr Pro Leu Pro
            35                  40                  45
```

(2) INFORMATION FOR SEQ ID NO:7:

(i) SEQUENCE CHARACTERISTICS:
    (A) LENGTH: 56 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (vi) ORIGINAL SOURCE:
    (A) ORGANISM: hirudo medicinalis
    (C) INDIVIDUAL ISOLATE: hirudin variant type PA (HV3)

(xi) SEQUENCE DESCRIPTION: SEQ ID NO:7:

```
Ile Thr Tyr Thr Asp Cys Thr Glu Ser Gly Gln Asn Leu Cys Leu Cys
 1               5                  10                  15

Glu Gly Ser Asn Val Cys Gly Lys Gly Asn Lys Cys Ile Leu Gly Ser
            20                  25                  30

Gln Gly Leu Asp Asn Gln Cys Val Thr Gly Glu Gly Thr Pro Leu Pro
            35                  40                  45

Gln Ser His Asn Gln Gly Asp Phe
            50              55
```

(2) INFORMATION FOR SEQ ID NO:8:

(i) SEQUENCE CHARACTERISTICS:
    (A) LENGTH: 57 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (vi) ORIGINAL SOURCE:
    (A) ORGANISM: hirudo medicinalis
    (C) INDIVIDUAL ISOLATE: hirudin variant type PA (HV3)

(xi) SEQUENCE DESCRIPTION: SEQ ID NO:8:

```
Ile Thr Tyr Thr Asp Cys Thr Glu Ser Gly Gln Asn Leu Cys Leu Cys
 1               5                  10                  15

Glu Gly Ser Asn Val Cys Gly Lys Gly Asn Lys Cys Ile Leu Gly Ser
            20                  25                  30

Gln Gly Leu Asp Asn Gln Cys Val Thr Gly Glu Gly Thr Pro Leu Pro
            35                  40                  45
```

Gln Ser His Asn Gln Gly Asp Phe Glu
            50                      55

( 2 ) INFORMATION FOR SEQ ID NO:9:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: hirudo medicinalis
        ( C ) INDIVIDUAL ISOLATE: hirudin variant type PA (HV3)

( x i ) SEQUENCE DESCRIPTION: SEQ ID NO:9:

Ile Thr Tyr Thr Asp Cys Thr Glu Ser Gly Gln Asn Leu Cys Leu Cys
    1               5                   10                  15

Glu Gly Ser Asn Val Cys Gly Lys Gly Asn Lys Cys Ile Leu Gly Ser
                20                  25                  30

Gln Gly Leu Asp Asn Gln Cys Val Thr Gly Glu Gly Thr Pro Leu Pro
                35                  40                  45

Gln Ser His Asn Gln Gly Asp Phe Glu Pro Ile Pro
            50                      55              60

( 2 ) INFORMATION FOR SEQ ID NO:10:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: hirudo medicinalis
        ( C ) INDIVIDUAL ISOLATE: hirudin variant type PA (HV3)

( x i ) SEQUENCE DESCRIPTION: SEQ ID NO:10:

Ile Thr Tyr Thr Asp Cys Thr Glu Ser Gly Gln Asn Leu Cys Leu Cys
    1               5                   10                  15

Glu Gly Ser Asn Val Cys Gly Lys Gly Asn Lys Cys Ile Leu Gly Ser
                20                  25                  30

Gln Gly Leu Asp Asn Gln Cys Val Thr Gly Glu Gly Thr Pro Leu Pro
                35                  40                  45

Gln Ser His Asn Gln Gly Asp Phe Glu Pro Ile Pro Glu Asp
            50                      55              60

( 2 ) INFORMATION FOR SEQ ID NO:11:

( i ) SEQUENCE CHARACTERISTICS:
        ( A ) LENGTH: 64 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO (i v) ANTI-SENSE: NO (v i) ORIGINAL SOURCE:
    (A) ORGANISM: hirudo medicinalis
    (C) INDIVIDUAL ISOLATE: hirudin variant type PA (HV3)

(i x) FEATURE:
    (A) NAME/KEY: Modified-site
    (B) LOCATION: 64
    (D) OTHER INFORMATION: /note="Tyr 64 is a modified Tyr
    (R) residue, wherein R is the phenolic
        hydroxygroup of Tyr (desulphatohirudin) or a
        O-SO3H group (x i) SEQUENCE DESCRIPTION: SEQ ID NO:11:

| Ile | Thr | Tyr | Thr | Asp | Cys | Thr | Glu | Ser | Gly | Gln | Asn | Leu | Cys | Leu | Cys |
|---|---|---|---|---|---|---|---|---|---|---|---|---|---|---|---|
| 1 | | | | 5 | | | | | 10 | | | | | 15 | |

| Glu | Gly | Ser | Asn | Val | Cys | Gly | Lys | Gly | Asn | Lys | Cys | Ile | Leu | Gly | Ser |
|---|---|---|---|---|---|---|---|---|---|---|---|---|---|---|---|
| | | | 20 | | | | 25 | | | | | | 30 | | |

| Gln | Gly | Leu | Asp | Asn | Gln | Cys | Val | Thr | Gly | Glu | Gly | Thr | Pro | Leu | Pro |
|---|---|---|---|---|---|---|---|---|---|---|---|---|---|---|---|
| | | 35 | | | | | 40 | | | | | 45 | | | |

| Gln | Ser | His | Asn | Gln | Gly | Asp | Phe | Glu | Pro | Ile | Pro | Glu | Asp | Ala | Tyr |
|---|---|---|---|---|---|---|---|---|---|---|---|---|---|---|---|
| | 50 | | | | | 55 | | | | 60 | | | | | |

(2) INFORMATION FOR SEQ ID NO:12:

(i) SEQUENCE CHARACTERISTICS:
        (A) LENGTH: 65 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v i) ORIGINAL SOURCE:
    (A) ORGANISM: hirudo medicinalis
    (C) INDIVIDUAL ISOLATE: hirudin variant type PA (HV3)

(i x) FEATURE:
    (A) NAME/KEY: Modified-site
    (B) LOCATION: 63
    (D) OTHER INFORMATION: /note="Tyr 63 is a modified Tyr
    (R) residue, wherein R is the phenolic
        hydroxygroup of Tyr (desulphatohirudin) or a
        O-SO3H group (x i) SEQUENCE DESCRIPTION: SEQ ID NO:12:

| Thr | Tyr | Thr | Asp | Cys | Thr | Glu | Ser | Gly | Gln | Asn | Leu | Cys | Leu | Cys | Glu |
|---|---|---|---|---|---|---|---|---|---|---|---|---|---|---|---|
| 1 | | | | 5 | | | | | 10 | | | | | 15 | |

| Gly | Ser | Asn | Val | Cys | Gly | Lys | Gly | Asn | Lys | Cys | Ile | Leu | Gly | Ser | Gln |
|---|---|---|---|---|---|---|---|---|---|---|---|---|---|---|---|
| | | | 20 | | | | 25 | | | | | | 30 | | |

| Gly | Leu | Asp | Asn | Gln | Cys | Val | Thr | Gly | Glu | Gly | Thr | Pro | Leu | Pro | Gln |
|---|---|---|---|---|---|---|---|---|---|---|---|---|---|---|---|
| | | 35 | | | | | 40 | | | | | 45 | | | |

| Ser | His | Asn | Gln | Gly | Asp | Phe | Glu | Pro | Ile | Pro | Glu | Asp | Ala | Tyr | Asp |
|---|---|---|---|---|---|---|---|---|---|---|---|---|---|---|---|
| | 50 | | | | | 55 | | | | 60 | | | | | |

| Glu |
|---|
| 65 |

(2) INFORMATION FOR SEQ ID NO:13:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) ORIGINAL SOURCE:
  (A) ORGANISM: hirudo medicinalis
  (C) INDIVIDUAL ISOLATE: hirudin variant type PA (HV3)

(ix) FEATURE:
  (A) NAME/KEY: Modified-site
  (B) LOCATION: 62
  (D) OTHER INFORMATION: /note="Tyr 62 is a modified Tyr
  (R) residue, wherein R is the phenolic
    hydroxygroup of Tyr (desulphatohirudin) or a
    O-SO3H group (xi) SEQUENCE DESCRIPTION: SEQ ID NO:13:

```
Tyr Thr Asp Cys Thr Glu Ser Gly Gln Asn Leu Cys Leu Cys Glu Gly
 1               5                   10                      15

Ser Asn Val Cys Gly Lys Gly Asn Lys Cys Ile Leu Gly Ser Gln Gly
            20                  25                  30

Leu Asp Asn Gln Cys Val Thr Gly Glu Gly Thr Pro Leu Pro Gln Ser
            35                  40              45

His Asn Gln Gly Asp Phe Glu Pro Ile Pro Glu Asp Ala Tyr Asp Glu
        50                  55                  60
```

MONOCLONAL ANTIBODIES DIRECTED AGAINST COMPLEXES FORMED BY THROMBIN AND HIRUDIN

The invention concerns monoclonal antibodies which are directed against the thrombin/hirudin-complex and derivatives thereof, processes for their preparation, hybridoma cell lines secreting said monoclonal antibodies, and processes for the preparation of the hybridoma cell lines. Furthermore, the invention relates to the use of the monoclonal antibodies and/or their derivatives for the determination of the thrombin/hirudin-complex as well as to test kits comprising said monoclonal antibodies and/or their derivatives.

BACKGROUND OF THE INVENTION

An efficiently operating haemostatic system is of vital necessity for the mammalian organism. In healthy organisms defects of the blood vascular system, e.g. vascular lesions, are repaired in a two-step process: the aggregation of thrombocytes is followed by the formation of a fibrin clot in an enzyme cascade under participation of several blood clotting factors. Most of these factors are serin proteases, for example thrombin which catalyzes the reaction of fibrinogen to fibrin. The coagulation system is counteracted by the fibrinolytic system involving, among others, the protease plasmin which cleaves fibrin. The coagulation and fibrinolytic systems are usually in a dynamic equilibrium. In cases, however, in which the fibrinolytic potential of the organism is disturbed or insufficient, for example in patients suffering from thromboembolisms or post-operative complications, it is indispensable to support the organism by the administration of anticoagulants to prevent further formation of fibrin and of thrombolytic agents to dissolve the formed thrombi.

Hirudin, an anticoagulant that occurs naturally in leeches (*Hirudo medicinalis*), is a potent and specific inhibitor of thrombin, preventing the cleavage of fibrinogen and subsequent fibrin clot formation. Hirudin reacts very rapidly with α-thrombin to form a very tight noncovalent complex ($K_I \approx 1$–0.01 pM) which is extremely stable and enzymatically totally inactive. Several closely related hirudin variants have been described, each containing 65 or 66 amino acids, for example the variants designated hirudin variant 1 (HV1), hirudin variant 2 (HV2), hirudin variant PA (HV3), and "des-(Val)$_2$-hirudin". The variants differ from each other by a number of amino acids, but all have an accumulation of hydrophobic amino acids at the N-terminus, an accumulation of polar amino acids at the C-terminus, a tyrosine residue (Tyr 63) present as sulphate monoester, three disulphide bridges and the anticoagulant activity in common. Recently, cDNAs and synthetic genes coding for hirudin variants have been cloned and expressed in microbial hosts. The recombinant hirudin variants lack the sulphate monoester group at Tyr 63 and are therefore also referred to as desulphatohirudins. However, they exhibit biological properties at least equivalent to those of natural sulphated hirudins.

Hirudin has a great potential for future therapeutic use due to its selective inhibition of thrombin in conjunction with its low toxicity and the absence of immunological side effects. However, the successful therapeutic application of hirudin also requires a system for monitoring its activity as well as the course of the therapy. In addition, it is desirable to be able to determine the actual requirement for hirudin treatment. A solution to these problems would be the development of antibodies against the complex formed by thrombin and hirudin which could be employed to detect the formation of thrombin even in small amounts.

OBJECT OF THE INVENTION

It is the object of the present invention to produce monoclonal antibodies which are directed against the thrombin/hirudin-complex. This object is achieved by using hirudin coupled to a suitable carrier or the thrombin/hirudin-complex to immunize a suitable mammal and fusing antibody-secreting cells of said mammal with cells of a continuous cell line, thus producing hybridoma cells which secrete the desired monoclonal antibodies. The monoclonal antibodies of the invention are useful for a number of diagnostic and therapeutic purposes, for example for the early detection of thrombin formation and thrombosis.

DESCRIPTION OF THE INVENTION

The invention concerns monoclonal antibodies directed against the thrombin/hirudin-complex, and derivatives thereof which retain the specificity of the antibody from which they are derived.

In the present application, the term hirudin, when not otherwise stated, is intended to embrace (1) all naturally occurring or synthetic hirudin variants and hirudin derivatives, such as hirudin fragments, and (2) all recombinant hirudin (desulphatohirudin) variants and recombinant hirudin (desulphatohirudin) derivatives, such as C-terminally shortened desulphatohirudins, which are described in the literature or are obtainable by methods of recombinant DNA technology.

Examples of such hirudins are:

(a) a hirudin variant of type HV1 with the formula (SEQ ID NO:1)

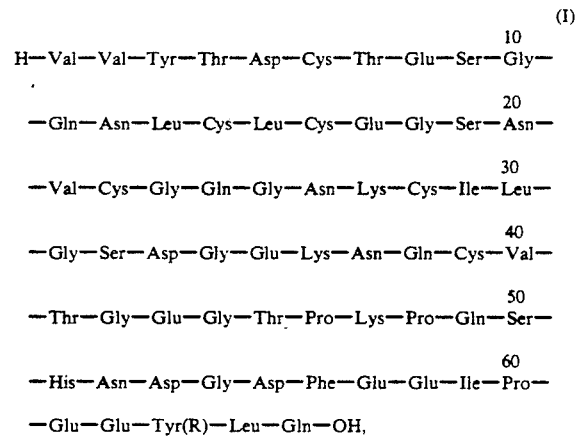

wherein
(R) is the phenolic hydroxygroup of Tyr (desulphatohirudin) or a —O—SO$_3$H group, and/or
Lys 27 is replaced by Ile or Glu or
Lys 36 is replaced by Ile or Glu or
Lys 47 is replaced by Ile or Glu or
His 51 is replaced by Leu or Asp or
Val 1-Val 2 are replaced by Thr or
Val 1 is replaced by Leu and Val 2 by Thr, or the whole molecule is shortened by Gln 65 (SEQ ID NO:2) or by Leu 64 and Gln 65 (SEQ ID NO:3);

(b) a hirudin variant of type HV2 with the formula (SEQ ID NO:4)

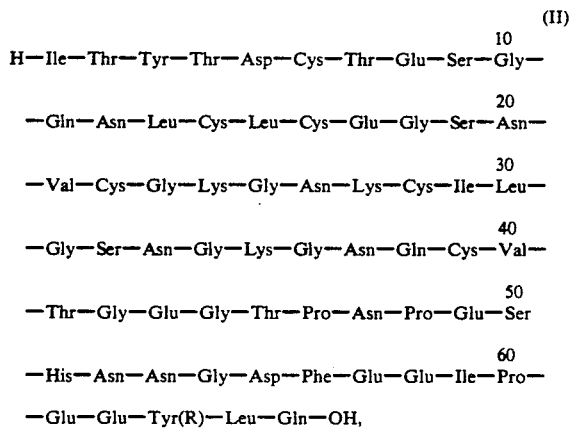

(II)

wherein
(R) is the phenolic hydroxygroup of Tyr (desulphatohirudin) or a —O—SO$_3$H group, and/or
Ile 1 is replaced by Val and Thr 2 by Val or
Asn 47 is replaced by Lys or Arg or His or
Tyr 63 is replaced by Glu or Asp;

(c) a hirudin variant of type PA (HV3) with the formula (SEQ ID NO:5)

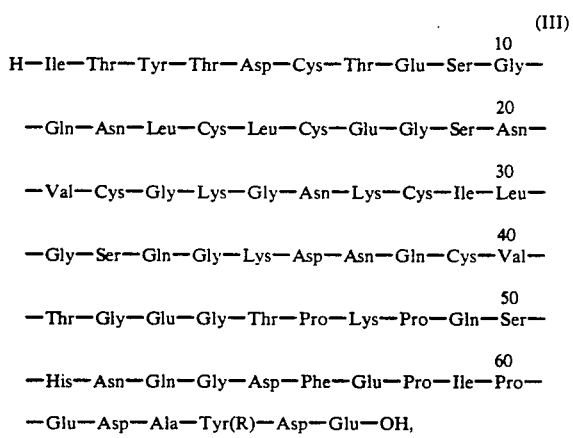

(III)

wherein
(R) is the phenolic hydroxygroup of Tyr (desulphatohirudin) or a —O—SO$_3$H group, and/or
the polypeptide chain is shortened at the C-terminus by 18 (SEQ ID NO:6), 10 (SEQ ID NO:7), 9 (SEQ ID NO:8), 6 (SEQ ID NO:9), 4 (SEQ ID NO:10), OR 2 (SEQ ID NO:11) amino acids, or
the polypeptide chain is shortened at the N-terminus by 1 (SEQ ID NO:12) OR 2 (SEQ ID NO:13) amino acids.

The monoclonal antibodies of the invention are tested for the desired properties, preferentially by a radio- or enzyme immunoassay. For example, an enzyme immunoassay is carried out wherein a suitable carrier such as a microtiter plate is coated with a suitable anti-α-thrombin monoclonal antibody, e.g. an anti-α-thrombin monoclonal antibody which does not interfere with the binding of hirudin to thrombin, and the thrombin/hirudin-complex. Then an enzyme labelled monoclonal antibody of the invention and a substrate solution are added, and the binding of the monoclonal antibody according to the invention is detected by determining the enzyme label of the immune complex bound to the carrier.

Preferred are monoclonal antibodies which are directed against the thrombin/hirudin-complex wherein hirudin is hirudin variant 1 (HV1), and derivatives thereof. Equally preferred are monoclonal antibodies which are directed against the thrombin/hirudin-complex wherein hirudin is recombinant hirudin (rHV), and derivatives thereof. Especially preferred are monoclonal antibodies which are directed against the thrombin/hirudin-complex wherein hirudin is recombinant hirudin variant 1 (rHV1), and derivatives thereof.

Since the thrombin/hirudin-complex contains the two components thrombin and hirudin, monoclonal antibodies reactive with the complex may recognize either the hirudin or the thrombin moiety of the complex, or a determinant encompassing parts of both moieties. Furthermore, anti-thrombin/hirudin-complex monoclonal antibodies may recognize so-called neo-determinants specific to the complex resulting from conformational changes occuring during the formation of the thrombin/hirudin-complex.

A preferred embodiment of the present invention concerns monoclonal antibodies which are directed against the thrombin/hirudin-complex and which recognize determinants of the hirudin moiety in the thrombin/hirudin-complex, and derivatives thereof. Preferred are monoclonal antibodies which are directed against the thrombin/hirudin-complex wherein hirudin is hirudin variant 1 (HV1) and which recognize determinants of the HV1 moiety in the complex. Also preferred are monoclonal antibodies which are directed against the thrombin/hirudin-complex wherein hirudin is recombinant hirudin (rHV) and which recognize determinants of the rHV moiety in the complex, and derivatives thereof. Particularly preferred are monoclonal antibodies which are directed against the thrombin/hirudin-complex wherein hirudin is recombinant hirudin variant 1 (rHV1) and which recognize the rHV1 moiety in the complex, and derivatives thereof. In this latter group of monoclonal antibodies, monoclonal antibodies which recognize determinants within the N-terminal core domain of the rHV1 moiety in the thrombin/rHV1-complex, preferentially determinants comprising the amino acid residues 1 to 43 of the rHV1 moiety, and derivatives thereof are especially preferred. An example of a particularly preferred monoclonal antibody and its derivatives is the monoclonal antibody designated MAb 4158-81-7 and derivates thereof.

Another preferred embodiment of the present invention concerns monoclonal antibodies which are directed against the thrombin/hirudin-complex and which recognize determinants of the thrombin moiety in the thrombin/hirudin-complex, and derivatives thereof. Preferred are monoclonal antibodies which are directed against the thrombin/hirudin complex wherein hirudin is hirudin variant 1 (HV1) and which recognize determinants of the thrombin moiety in the complex. Also preferred are monoclonal antibodies which are directed against the thrombin/hirudin-complex wherein hirudin is recombinant hirudin (rHV) and which recognize determinants of the thrombin moiety in the complex, and derivatives thereof. Particularly preferred are monoclonal antibodies which are directed against the thrombin/hirudin-complex wherein hirudin is recombinant hirudin variant 1 (rHV1) and which recognize the thrombin moiety in the complex, and derivatives thereof. In this latter group of monoclonal antibodies, monoclonal antibodies which recognize determinants of the thrombin moiety which become exposed for antibody binding only when thrombin is bound to hirudin or to a solid surface but do not recognize free thrombin in solution, and derivatives thereof, are especially preferred. An example of a particularly preferred monoclonal antibody and its derivatives is the monoclonal antibody designated MAb 4107-76-1 and derivates thereof.

Derivatives of a monoclonal antibody of the invention retain the specificity of the antibody from which they are derived, i.e. they retain the characteristic binding pattern of the parent antibody. Examples of such derivatives are conjugates of the monoclonal antibodies with an enzyme, a fluorescent marker, a chemiluminescent marker, a metal chelate, paramagnetic particles, avidin, biotin or the like, or radioactively labelled monoclonal antibodies, or monoclonal antibody fragments.

Enzymes used for antibody conjugates of the invention are, for example, horseradish peroxidase, alkaline phosphatase, $\beta$-D-galactosidase, glucose oxidase, glucoamylase, carbonic anhydrase, acetylcholinesterase, lysozyme, malate dehydrogenase or glucose-6-phosphate dehydrogenase.

Fluorescent markers conjugated with antibodies of the invention can be fluorescein, fluorochrome, rhodamine, and the like.

Chemiluminescent markers are organic molecules which emit light upon chemical structure modification, e.g. luminol, isoluminol, pyrogallol, luciferin, and the like.

Examples of metal chelates are ethylenediaminetetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like.

In such conjugates, the antibody is bound to the conjugation partner directly or by way of a spacer or linker group.

Radioactively labelled antibodies of the invention contain e.g. radioactive iodine ($^{123}$I, $^{125}$I, $^{131}$I), tritium ($^{3}$H), carbon ($^{14}$C), sulfur ($^{35}$S), yttrium ($^{90}$Y), technetium ($^{99m}$Tc), or the like.

Antibody fragments of the invention are for example the fragments Fab, Fab', or F(ab')$_2$.

The monoclonal antibodies of the invention and derivatives thereof are obtained by processes known per se wherein cells of a hybridoma cell line secreting the desired monoclonal antibodies are multiplied in vitro or in vivo and, when required, the obtained monoclonal antibodies are isolated and/or converted into derivatives thereof.

Multiplication in vitro is carried out in suitable culture media, which are the customary standard culture media, for example Dulbecco's Modified Eagle Medium (DMEM) or RPMI 1640 medium, optionally replenished by a mammalian serum, e.g. fetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like.

In vitro production provides relatively pure antibody preparations and allows scale-up to give large amounts of the desired antibodies. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

For isolation of the monoclonal antibodies, the immunoglobulins in the culture supernatants are first concentrated, e.g. by precipitation with ammonium sulphate, dialysis against hygroscopic material such as polyethylene glycol (PEG), filtration through selective membranes or the like. If necessary and/or desired, the concentrated antibodies are purified by customary chromatography methods, for instance gel filtration, ion exchange chromatography, chromatography over DEAE-cellulose or Protein A, or immunoaffinity chromatography.

Large quantities of the desired monoclonal antibodies can also be obtained by multiplying the cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethylpentadecane), prior to the injection. After one to three weeks, the antibodies are isolated from the body fluids of those mammals. For example, hybridoma cells derived from Balb/c mice that produce the desired monoclonal antibodies are injected intraperitoneally into Balb/c mice optionally pre-treated with pristane, and, after one to two weeks, ascitic fluid is taken from the animals.

Conjugates of monoclonal antibodies of the invention are prepared by methods known in the art, e.g. by reacting an antibody prepared as described above in the presence of a coupling agent, e.g. glutaraldehyde, periodate, N,N'-o-phenylenedimaleimide, N-(m-maleimidobenzoyloxy)-succinimide, N-(3-[2'-pyridyldithio]-propionoxy)succinimide, N-ethyl-N'-(3-dimethylaminopropyl)-carbodiimide or the like. Conjugates with biotin are prepared e.g. by reacting antibodies with an activated ester of biotin such as the biotin N-hydroxysuccinimide ester. Conjugates with fluorescent or chemiluminescent markers are prepared in the presence of a coupling agent, e.g. those listed above, or by reaction with an isothiocyanate, preferably fluorescein-isothiocyanate.

Monoclonal antibodies radioactively labelled with iodine ($^{123}$I, $^{125}$I, $^{131}$I) are obtained from the antibodies of the invention by iodination known per se, for example with radioactive sodium or potassium iodide and a chemical oxidizing agent, such as sodium hypochlorite, chloramine T or the like, or an enzymatic oxidizing agent, such as lactoperoxidase or glucose oxidase and glucose. Antibodies according to the invention are labelled with yttrium ($^{90}$Y) for example by diethylenetriaminepentaacetic acid (DPTA)-chelation. Technetium-99m labelled antibodies are prepared by ligand exchange processes, for example by reducing pertechnate (TcO$_4^-$) with stannous ion solution, chelating the reduced technetium onto a Sephadex column and applying the antibodies to this column, or by direct labelling techniques, e.g. by incubating pertechnate, a reducing agent such as SnCl$_2$, a buffer solution such as sodium potassium phthalate solution, and the antibodies.

Fragments of the monoclonal antibodies according to the invention, for example Fab, Fab' or F(ab')$_2$ fragments, can be obtained from the monoclonal antibodies prepared as described above by methods known per se, e.g. by digestion with enzymes such as papain or pepsin and/or cleavage of disulfide bonds by chemical reduction.

The invention further concerns hybridoma cell lines which secrete the monoclonal antibodies of the invention, in particular hybridoma cell lines which secrete monoclonal antibodies directed against the thrombin/HV1-complex or the thrombin/rHV-complex, preferentially the thrombin/rHV1-complex.

In particular, the invention concerns hybridoma cell lines secreting the desired antibodies which are hybrids of myeloma cells and B lymphocytes of a mammal immunized with hirudin coupled to a suitable carrier or the thrombin/hirudin complex. Suitable mammals and carriers are described in detail hereinbelow. Preferred are hybridoma cell lines according to the invention which are hybrids of mouse myeloma cells and B lymphocytes of a mouse immunized with recombinant hirudin variant 1 (rHV1) coupled to a suitable carrier or the thrombin/rHV1 complex.

Particularly preferred are the hybridoma cell lines designated 4158-81-7 and 4107-76-1 which were deposited at the European Collection of Animal Cell Cultures (ECACC), PHLS Centre for Applied Microbiology & Research, Porton Down, Salisbury, Wilts, SP4 OJG, U.K., under the deposition number 90061405 and 90061404, respectively, on Jun. 14, 1990.

The hybridoma cell lines of the invention are genetically stable, secrete the monoclonal antibodies of the invention with constant specificity and may be kept in deep-frozen cultures and reactivated by thawing and optionally re-cloning.

The invention also concerns a process for the preparation of hybridoma cell lines secreting the monoclonal antibodies of the invention wherein a suitable animal is immunized with hirudin coupled to a suitable carrier or with the thrombin/hirudin-complex, antibody producing cells of the mouse are fused with cells of a continuous cell line, the hybrid cells obtained in the fusion are cloned, and cell clones secreting the desired monoclonal antibodies are selected.

The immunogen used to elicit the monoclonal antibodies of the invention is an immunogenic conjugate of hirudin, in particular of hirudin variant HV1, of recombinant hirudin (rHV), or preferentially of recombinant hirudin variant HV 1 (rHV1), or the thrombin/hirudin-complex, in particular the thrombin/HV1-complex, or the thrombin/rHV-complex, or preferentially the thrombin/rHV1 complex.

The coupling of hirudin to a carrier to form an immunogenic hirudin-conjugate is necessary to enhance the immunogenicity of hirudin which is only a weak immunogen by itself.

Suitable carrier molecules are for example lysine rich proteins with free amino groups available for coupling, especially high molecular weight proteins like bovine serum albumin (BSA; MW 66,200), alpha-amylase from *Bacillus subtilis* (MW 58,000) or keyhole limpet haemocyanin (KLH; MW>1,000,000) which are commercially available in large quantities. Porcine thyroglobulin, toxins such as tetanus-, cholera-or diphteriatoxins, human serum albumin (HSA), beta-2 -microglobulin, and the like, may also be used as carriers. Purified rabbit IgG fraction against mouse IgG(H+L) (Kawamura & Berzofsky, J. Immunol. 136, 58, 1986) may also be employed as a carrier. Other possible carrier molecules include polysaccharides, natural or synthetic lipopolysaccharides, synthetic polypeptides such as polylysine, activated membranes, latex particles, bacteria such as Salmonella, and the like.

Preferred is an immunogenic hirudin-conjugate, in which hirudin, particularly hirudin variant HV1, is coupled to keyhole limpet haemocyanin (KLH). Particularly preferred is an immunogenic hirudin-conjugate in which recombinant hirudin, particularly recombinant hirudin variant HV1 (rHV1), is coupled to KLH.

The hirudin-conjugates are prepared by methods known per se, either by adsorption of hirudin to the carrier or by coupling using periodate, glutaraldehyde, carbodiimides e.g. N,N'-o-phenylenedimaleimide, N-(m-maleimidobenzoyloxy)-succinimide, N-(3-[2'-pyridyldithio]-propionoxy)-succinimide, N-ethyl-N'-(3-dimethylaminopropyl)carbodiimide or the like. If coupling via carboxyl groups is intended, the amino groups of hirudin may first be protected, e.g. by acylation, for example with acetyl or tertiary butoxycarbonyl groups.

The thrombin/hirudin-complex used for immunization is prepared by mixing hirudin with thrombin, in particular by mixing an excess of hirudin with thrombin. The thrombin/hirudin-complex can be separated from free hirudin for example by gel filtration high pressure liquid chromatography (HPLC).

The immunogenic hirudin-conjugate or the thrombin/hirudin-complex may be mixed with adjuvants, i.e. agents that will further increase the immune response, for the immunization procedure. Possible adjuvants are Freund's complete adjuvant (emulsion of mineral oil, water, and mycobacterial extracts), Freund's incomplete adjuvant (emulsion of water and oil only), mineral gels, e.g. aluminium hydroxide gels, surface active substances such as lysolecithin, polyanions, peptides, BCG (Bacillus Calmette-Guerin), etc.

The immunogens are used to immunize suitable mammals which recognize them as foreign molecules, for example mice, rats, rabbits, donkeys, goats, sheep, horses, pigs or chimpanzees, especially mice or rats, preferentially mice. Particularly preferred are Balb/c mice.

The routes of immunization include, among others, intradermal, subcutaneous, intramuscular, intraperitoneal, intravascular and intracranial injections. Since high antibody titers are desired, a series of injections is commonly given. The immunization is for example performed by injecting the immunogenic hirudin-conjugate, optionally mixed with incomplete or complete Freund's adjuvant, three to eight times parenterally, e.g. intraperitoneally and/or subcutaneously, in amounts of 10–50 $\mu$g into Balb/c mice at intervals of 1–3 weeks, followed by a booster injection of about 50–500 $\mu$g 1–3 months after the last immunization.

Antibody-producing cells of the immunized mice, preferably lymphoid cells such as spleen lymphocytes, taken for example one to five days after the final injection, are fused with the cells of a continuous cell line, i.e. a continuously replicating cell clone which confers this replication ability to the hybrid cells resulting from the fusion. An example for such a cell line is a tumour cell line (myeloma) which does not itself actually produce immunoglobulins or fragments thereof but has the potential to produce and secrete large amounts of antibody, and which carries a genetic marker so that the hybrid cells can be selected against non-fused parent cells. Several suitable myeloma cell lines are known in the art. Preferred are myeloma cell lines lacking the enzyme hypoxanthine guanine phosphoribosyl transferase (HGPRT) or the enzyme thymidine kinase (TK), which therefore do not survive in a selective culture medium containing hypoxanthine, aminopterin and thymidine (HAT medium). Particularly preferred are myeloma cells and derived cell lines that do not survive in HAT medium and do not secrete immunoglobulins or fragments thereof, particularly the mouse myeloma cell lines Sp2/0-Ag14 (Shulman et al., Nature 276, 269, 1978) or X63-Ag8.653 (Kearney et al., J. Immunol. 123, 1548, 1979) which are commercially available (Flow), or the mouse myeloma cell line PAI (Stocker et al., Research Disclosure No. 21713, 1982).

The fusion is performed in the presence of a fusion promoter, for example Sendai virus or other paramyxo viruses, optionally in UV-inactivated form, or chemical fusogens such as calcium ions, surface-active lipids, e.g. lysolecithin, or polyethylene glycol (PEG), or by electrofusion. Preferentially, the myeloma cells are fused with a three- to twentyfold excess of spleen cells from immunized mammals in a solution containing about 30% to about 60% of polyethylene glycol of a molecular weight between 1000 and 4000.

After the fusion, the cells are resuspended and cultivated in a selective medium chosen depending on the genetic selection marker, for example HAT medium. In this medium, only hybridoma cells will survive, because they combine the ability to grow and replicate in vitro inherited from the parent myeloma cells and the missing HGPRT or TK genes essential for the survival in HAT medium inherited from the antibody-producing spleen cells of the immunized mammals.

Suitable culture media for the expansion of hybridoma cells are the standard culture media, such as Dulbecco's Modified Eagle Medium (DMEM), minimum essential medium, RPMI 1640 and the like, optionally replenished by a mammalian serum, e.g. 10 to 15% fetal calf serum. Preferentially, feeder cells, e.g. normal mouse peritoneal exudate cells, spleen cells, bone marrow macrophages or the like, are added at the beginning of cell growth immediately after the fusion step to nourish the hybridoma cells and support their growth, especially where cell densities are low, by providing growth factors and the like. If phagocytic cells such as macrophages or monocytes are used, they can perform a helpful service in cleaning up the debris of dead myeloma cells always found after aminopterin treatment. The culture media are supplemented with selective medium in order to prevent myeloma cells from overgrowing the hybridoma cells.

The hybridoma cell culture supernatants are screened for the desired monoclonal antibodies with an immunoassay, preferentially a radio- or enzyme immunoassay. For example, a suitable carrier such as a microtiter plate is coated with the thrombin/hirudin-complex and incubated with the hybridoma supernatant to be tested. Then, enzyme labelled antibodies which recognize the antibodies bound to the thrombin/hirudin-complex on the carrier and a substrate solution are added, and the labelled antibodies bound to the antibody-thrombin/hirudin-complex are detected by determining the enzyme label bound to the carrier.

Positive hybridoma cells are cloned, e.g. by limiting dilution or in soft agar, preferentially twice or more. Optionally, hybridoma cells are passaged through animals, e.g. mice, by intraperitoneal injection and harvesting of ascites, which stabilizes hybridomas and improves growth characteristics. The cloned cell lines may be frozen in a conventional manner.

The monoclonal antibodies of the invention and their derivatives are useful for a number of in vitro and in vivo medical purposes, all of which are based on the qualitative and/or quantitative determination of the thrombin/hirudin-complex. In particular, the monoclonal antibodies of the invention and derivatives thereof can be employed for the early diagnosis of thrombosis, especially in high risk groups and patients with thrombotic disorders. This is achieved by detection of small amounts of spontaneously generated thrombin by injecting hirudin as a tracer followed by the measurement of the complex formed, thus determining the moment when hirudin treatment is necessary or preventive hirudin therapy would be advisable. In addition, the monoclonal antibodies of the invention and their derivatives are useful for the monitoring of hirudin therapy by determining hirudin activity, for establishing the correct hirudin dosage, and for recording possible progression of the disease.

For the quantitative determination of the thrombin/hirudin-complex, the monoclonal antibodies of the invention and/or their derivatives can for instance be used in any of the known immunoassays which rely on the binding interaction between the antigenic determinants of the thrombin/hirudin-complex molecule and the paratopes of the monoclonal antibodies. Examples of such assays are radio-, enzyme, fluorescence, chemiluminescence, immunoprecipitation, latex agglutination, and hemagglutination immunoassays, laser light scattering or evanescent light tests.

The monoclonal antibodies of the invention can be used as such or in the form of radioactively labelled derivatives in a radioimmunoassay (RIA). Such immunoassays also include test procedures in which radioactively labelled antibodies known per se that recognize and bind an epitope of the antibodies of the invention are used. Any of the known modifications of a RIA can be used, for example soluble phase (homogeneous) RIA, solid phase (heterogeneous) RIA, single RIA or double (sandwich) RIA with direct or indirect (competitive) determination of the thrombin/hirudin-complex.

Preferred is a sandwich RIA in which a suitable carrier, for example the plastics surface of a microtiter plate or of a test tube, e.g. of polystyrene, polypropylene or polyvinyl chloride, glass or plastic beads, filter paper, dextran etc., cellulose acetate or nitrocellulose sheets, magnetic particles, or the like, is coated with a monoclonal antibody of the invention, preferentially MAb 4107-76-1. Then test solutions, for example plasma from a patient, which contain the thrombin/hirudin-complex, and finally second polyclonal or monoclonal antibodies which recognize a different epitope of the antigen than the first carrier-bound monoclonal antibody and which are radioactively labelled, e.g. with $^{125}$I, preferentially radioactively labelled monoclonal antibodies of the invention such as MAb 4158-81-7, are added. The amount of the thrombin/hirudin-complex in the test solution is directly proportional to the amount of bound second antibodies and is determined by measuring the radioactivity bound to the carrier.

The monoclonal antibodies according to the invention can be used as such or in the form of enzyme-conjugated derivatives in an enzyme immunoassay. Such immunoassays also include test procedures in which enzyme-labelled antibodies known per se that recognize and bind an epitope of the antibodies of the invention are used. As described above for radioimmunoassays, any of the known modifications of an enzyme immunoassay can be used.

The tests are carried out in an analogous manner to the radioimmunoassays described above using an enzyme label instead of a radioactive label. The amount of immune complex formed which corresponds to the amount of the thrombin/hirudin-complex present in the test solutions is determined by adding an enzyme substrate solution. The enzyme substrate reaction results, for example, in a color change which can be observed by eye or with optical measuring devices.

There is preferred an enzyme-linked immunosorbent assay (ELISA) in which a carrier as described above for a RIA is coated with a monoclonal antibody of the invention, preferentially MAb 4107-76-1, incubated with test solutions containing the thrombin/hirudin-complex, with polyclonal or monoclonal second antibodies which recognize a different epitope of the antigen than the first carrier-bound monoclonal antibody and which are enzyme-conjugated, preferentially enzyme-conjugated monoclonal antibodies of the invention such as MAb 4158-81-7, and with a substrate solution. The enzyme substrate reaction results, for example, in a colour change and can be observed by eye or with optical measuring devices, so that the amount of bound enzyme, which is proportional to the amount of the thrombin/hirudin-complex in the test solution, can be determined. An alternative is an enzyme immunoassay which is carried out essentially as described above but wherein the first carrier-bound monoclonal antibody of the invention is coupled to a small chemical group such as biotin and is detected by a labelled reagent, e.g. a biotin binding protein such as avidin or streptavidin.

The monoclonal antibodies according to the invention can be used as such or in the form of derivatives conjugated with chemiluminescent markers in a chemiluminescence immunoassay. Such immunoassays also include test procedures in which antibodies known per se that recognize and bind an epitope of the antibodies of the invention and which are conjugated with chemiluminescent markers are used. As described above for radioimmunoassays, any of the known modifications of a chemiluminescence immunoassay can be used.

The tests are carried out in an analogous manner to the radioimmunoassays described above using a chemiluminescent label instead of a radioactive label. The amount of immune complex formed which corresponds to the amount of antibodies directed against the thrombin/hirudin-complex present in the test solutions is determined by adding a compound triggering luminescence, e.g. $H_2O_2$ and NaOH, and measuring the emission of light with optical measuring devices.

The use according to the invention of monoclonal antibodies and derivatives thereof as described hereinbefore for the qualitative and quantitative determination of the thombin/hirudin-complex also includes other immunoassays known per se, for example immunofluorescence assays using antibodies or antibody derivatives conjugated with fluorescent markers such as fluorescein, latex agglutination with antibody-coated or antigen-coated latex particles, hemagglutination with antibody-coated or antigen-coated red blood corpuscles, evanescent light wave assays using an antibody-coated optical fibre and other direct-acting immunosensors which convert the binding event into an electrical or optical signal, or the like.

The application of the monoclonal antibodies of the invention and/or derivatives thereof in the above-described assays allows the determination of the presence and/or the concentration of the thrombin/hirudin-complex in buffer, urine and plasma in concentrations ranging from 1 to 200 ng/ml.

The invention also concerns test kits for the qualitative and quantitative determination of the thrombin/-hirudin-complex comprising monoclonal antibodies of the invention and/or derivatives thereof and, optionally, other monoclonal or polyclonal antibodies and/or adjuncts.

Test kits according to the invention for a radioimmunoassay contain, for example, a suitable carrier, e.g. microtiter plates or nitrocellulose sheets, uncoated or coated with a monoclonal antibody of the invention, optionally freeze-dried or concentrated solutions of a second radiolabelled antibody directed against a different epitope the thrombin/hirudin-complex than the first carrier-bound monoclonal antibody and/or a radiolabelled derivative thereof, standard solutions of the thrombin-hirudin-complex, buffer solutions and, optionally, polypeptides and detergents for preventing non-specific adsorption and aggregate formation, pipettes, reaction vessels, calibration curves, instruction manuals and the like.

Test kits according to the invention for an enzyme immunoassay contain, for example, a suitable carrier, uncoated or coated with a monoclonal antibody of the invention, optionally freeze-dried or concentrated solutions of a second enzyme-labelled antibody directed against a different epitope of the thrombin/hirudin-complex than the first carrier-bound monoclonal antibody and/or an enzyme-labelled derivative thereof, enzyme substrates in solid or dissolved form, standard solutions of the thrombin/hirudin-complex, buffer solutions and, optionally, polypeptides and detergents for preventing non-specific adsorption and aggregate formation, pipettes, reaction vessels, calibration curves, instruction manuals and the like.

The following examples illustrate the invention, but do not limit it to any extent.

Abbreviations

HAT-hypoxanthine/aminopterin/thymidine
HPLC-high pressure liquid chromatography
MAb-monoclonal antibody
MES-2-[N-morpholino]ethane-sulfonic acid
PBS-phosphate buffered saline
PEG-polyethylene glycol
rHV1-recombinant hirudin variant HV1
RT-room temperature
THC-thrombin/hirudin-complex

EXAMPLES

Example 1

Preparation of monoclonal antibodies against the thrombin/hirudin-complex 1.1 Preparation of the immunogens As immunogens are used: (1) a conjugate of recombinant hirudin variant HV1 (rHV1) with keyhole limpet hemacyanin (KLH), and (2) the thrombin/rHV1-complex.

rHV1 (Plantorgan/Ciba-Geigy) is coupled to KLH (Calbiochem) by the carbodiimide method as described in the following: 2 mg of rHV1 in 560 μl of 0.1M MES buffer pH 4.75 are mixed with 100 μl of KLH (10 mg/ml) and 200 μl of N-ethyl-N'-(3-dimethylamino-propyl)-carbodiimide hydrochloride (20 mg/ml). After 2 h at 22° C., the mixture is dialyzed in PBS.

The thrombin/rHV1-complex is prepared by mixing an excess of rHV1 with thrombin in PBS (1.7:1 molar ratio).

1.2 Immunization protocol

Two groups of five Balb/c female mice (4–6 weeks old) are given three series of injections with KLH-conjugated rHV1 (30 μg/injection; group I) or with the thrombin/rHV1 complex (15 μg/injection; group II). The first injection consists of 0.1 ml of the respective immunogen in PBS mixed in a 1:1 ratio with 0.1 ml of complete Freund's adjuvant (Difco); 50 μl are injected intraperitoneally and 150 μl subcutaneously. In the second (day 14) and third (day 30) series of injections, complete Freund's adjuvant is replaced by incomplete Freund's adjuvant. One week after the last injection, serum is collected and antibody titers are determined by an enzyme-linked immunosorbent assay (ELISA) as described in example 1.3.

1.3 Enzyme-linked immunosorbent assay (ELISA) for determination of serum antibody titer The antibody titers in the sera are determined by an ELISA as described in the following.

A twofold molar excess of thrombin is mixed with rHV1 (0.2 μg and 0.02 μg/well, respectively). Microtiter plates (Dynatech) are coated with 100 μl per well of a solution of the thrombin/rHV1-complex in coating buffer (50 mM sodium carbonate buffer pH 9.6: 477 mg $Na_2CO_3$, 879 mg $NaHCO_3$, 1.8 ml $NaN_3$ 0.5M, ad 300 ml $H_2O$). The plates are incubated overnight at 4° C. in a moist chamber and washed five times with PBS-Tween 0.1% (1 ml Tween-20, Serva, 1000 ml PBS). The wells are allowed to dry, filled with 200 ml per well of PBS-BSA 1% (1 g BSA, 3 ml $NaN_3$ 0.5M, ad 100 ml PBS), incubated for 2 h at RT and washed five times with PBS-Tween 0.1%. Then, 100 μl of the respective serum diluted in PBS-Tween 0.1% are added to each well. After 2 h incubation at RT, the plates are washed five times with PBS-Tween 0.1%. In the next step, 100 μl of alkaline phosphatase affinity purified goat antibody to mouse IgG (Kirkegaard & Perry Laboratories) diluted 1:1500 in PBS-Tween 0.1% are added to each well. The plates are incubated for 1.5 h at RT and are washed five times with PBS-Tween 0.1%. Finally, 150 μl per well of substrate solution (1 mg p-nitrophenylphosphate [Sigma] per ml diethanolamine buffer pH 9.8: 97 ml diethanolamine [Merck], 6 ml $NaN_3$ 0.5M, 100 mg $MgCl_2.6H_2O$, adjusted to pH 9.8 with HCl conc., ad 1000 ml $H_2O$) are added, the reaction is stopped by adding 50 μl of NaOH 3M, and the optical density is read at 405 nm after 2 h incubation at RT in the dark.

1.4 Fusion protocol

After a rest period of more than two months, the mice are boosted intraperitoneally with either 300 μg of rHV1-KLH-conjugate (group I) or 70 μg of the thrombin/rHV1-complex (group II). Three to four days later, the mice are sacrificed, the spleen cells are fused with the murine myeloma cell line PAI (Stocker et al., Research Disclosure No. 21713, p. 155, 1982), using PEG 4000 (Merck), by a modification of the original Köhler and Milstein method (Galfre et al., Nature 266, 550, 1977), and the cells are distributed into microtiter plate wells containing HAT medium (Boehringer). After 2 to 4 weeks, wells containing growing hybridomas are tested for specific monoclonal antibodies by ELISA of example 1.5.

1.5 Enzyme-linked immunosorbent assay (ELISA) for hybridoma screening

The growing hybridomas are tested for the presence of specific antibodies by an ELISA an described in Example 1.3. Instead of sera, 200 μl of hybridoma cell supernatants diluted 1:2 in PBS-Tween 0.1% are added to the microtiter plates coated with the thrombin/rHV1-complex.

From three fusions performed with the mice of group I (fusion efficiency 100%), six hybridomas secreting MAbs reactive with the thrombin/rHV1-complex are obtained. The three fusions with the mice of group II result in four such hybridomas, one of which secretes MAbs which crossreact with rHV1, whereas the MAbs secreted by the remaining three hybridomas crossreact with thrombin. Two hybridoma cell lines, one from each group, are selected for further characterization of the secreted MAbs. Both cell lines have been deposited on Jun. 14, 1990, at the European Collection of Animal Cell Cultures (ECACC), under the deposition numbers 90061405 for hybridoma 4158-81-7 (group I) and 90061404 for hybridoma 4107-76-1 (group II). The monoclonal antibodies secreted by these hybridomas are designated by the prefix "MAb" and the internal number of the respective hybridoma, e.g. MAb 4107-76-1.

1.6 Hybridoma storage and processing

The selected hybridoma cells can be grown in culture, frozen at −80° C. and kept in liquid nitrogen and then reactivated. The cells are cloned by the method of limiting dilution (J. W. Goding, J. Immunol. Methods 39, 285, 1980) and expanded by forming ascites in Balb/c mice primed with pristane (see example 2.1).

Example 2

Production, isolation and purification of the monoclonal anti-THC antibodies 2.1 Expansion of hybridomas in vivo and purification of the monoclonal antibodies For ascites production, female Balb/c mice (20–25 g) (Tierfarm Sisseln, Switzerland) are pretreated with 0.3 ml pristane oil (Aldrich) intraperitoneally. 1 to 3 weeks later, the mice receive a second injection of pristane (0.2 ml i.p.) and are simultaneously inoculated i.p. with $2\times10^6$ hybridoma cells in 0.2 ml PBS. After 8–10 days, the resulting ascites fluid is collected, centrifuged at 800 g and stored at −20° C. or at −80° C.

Defrosted ascites fluid is clarified by centrifugation at 30,000 g for 1 h. After removing the top layer containing lipids, the protein concentration is determined and adjusted to 10–12 mg/ml with PBS. The immunoglobulin G fraction (IgG) is precipitated by dropwise addition of 0.9 volumes of saturated ammonium sulfate at 0° C. After 1 h, the IgG fraction is pelleted by centrifugation for 1 h at 22,000 g. The pellet is dissolved in 20 mM Tris-HCl buffer pH 7.9 containing 50 mM NaCl, and is dialyzed against the same buffer overnight at 4° C. The IgG fraction is further purified by anion exchange chromatography on a column of DE52 diethylaminoethyl cellulose (Whatman). The sample is diluted 1:2 (v/v) in 20 mM Tris-HCl pH 7.9 to a final concentration of 25 mM NaCl, and 10 mg of protein per ml of gel are loaded onto the column. The elution is obtained by increasing the sodium chloride concentration from 25 mM to 200 mM (linear gradient). In general, MAbs are eluted around 80 mM NaCl. The fractions are dialyzed against PBS overnight at 4° C. and stored at −70° C. Purity is assessed by SDS-PAGE and isoelectric focusing. Purity is more than 90%.

2.2 Expansion of hybridomas in vitro

A preculture of any of the cell lines is obtained by culturing hybridoma cells at physiological temperature (around 37° C.) in RPMI 1640 medium (Seromed) containing 10% foetal calf serum (FCS) to a final cell density of $5 \times 10^5$ to $10^6$ cells per ml. The whole preculture is filled into Bellco culture vessels and adjusted to a total volume of 1500 ml with fresh RPMI 1640 medium/10% FCS. The culture is stirred at around 37° C. under 5% $CO_2$ at 30 rpm for two to three days, then diluted to a total volume of 3000 ml with RPMI 1640/10% FCS and stirred for another seven to ten days. After this time, 95% of the cells are dead. The culture broth is centrifuged at $1000 \times g$ for 20 min at 4° C. The supernatant is filtered through a filter with pore size 0.2 μm under sterile conditions. Crude immunoglobulin is precipitated by slow dropwise addition of 0.9 volume equivalents of saturated ammonium sulfate at 0° C. This precipitate is purified as described in Example 2.1.

Example 3

Determination of class and subclass of the monoclonal anti-THC antibodies

The class and subclass of the monoclonal antibodies is determined in an enzyme-linked immunosorbent assay (ELISA) kit from Bio-Rad. MAb 4158-81-7 and MAb 4107-76-1 are of class IgG1.

Example 4

Preparation of rHV1 analogues 4.1 Preparation of synthetic rHV1 peptides

Synthetic rHV1 peptides representing sequences 52–65, 40–65, 29–38, and 1–15 are synthesized by the solid phase method known in the art (Rink, Tetrahedron Letters 28, 3787, 1987). The rHV1 peptide representing the sequence 1–43 is synthesized as described in Chang et al., FEBS Letters 260, 209, 1990.

4.2 Reductive S-carboxymethylation

Reductive S-carboxymethylation of rHV1 is carried out according to Hirs (Methods in Enzymol. 11, 199, 1967). It results in the complete destruction of the three-dimensional structure of rHV1.

4.3 Digestion of rHV1 by V8 staphylococcal protease

70 μg of native rHV1 dissolved in 90 μl of $(NH_4)HCO_3$ buffer 50 mM, pH 8.0, supplemented with EDTA 2 mM, are mixed with 20 μg (in 20 μl) of *Staphylococcus aureus* strain V8 protease (Sigma), and incubated for either 30 min, 2 h or 4 h at 37° C. The reaction is stopped by the addition of 5 μl of diisopropylfluorophosphate 0.01M (Sigma). The extent of digestion is assessed by reverse-phase HPLC as described by Schlaeppi et al. (Eur. J. Biochem. 188, 463, 1990), or by amino-terminal analysis (Chang, Analytical Biochem. 170, 542, 1988), and by SDS-PAGE.

4.4 Digestion of rHV1 by lysyl endopeptidase

To 70 μg rHV1 dissolved in 97.5 μl 25 mM Tris/HCl pH 8.3, 2.5 μg in 2.5 μl lysysl endopeptidase (Wako Chemicals) are added and incubated for different periods of time at 37° C. The proteolytic fragments are separated by HPLC as described by Schlaeppi et al. (loc. cit.), and the extent of digestion is determined by quantitative N-terminal analysis.

Example 5

Test procedures used for the characterization of the anti-THC monoclonal antibodies 5.1 Biotinylation of rHV1, thrombin and the monoclonal antibodies Thrombin (1.1 nmol in 40 μl PBS) is mixed with biotin-X-N-hydroxysuccinimide ester (4.4 nmol in 2 μl DMSO) for 3 h at 4° C. Then 360 μl PBS are added before overnight dialysis against PBS.

Biotinylation of the MAbs is carried out essentially as described by Bayer et al. (Methods Enzymol. 62, 308, 1979). Biotin-X-N-hydroxysuccinimide ester (200 μg in 200 μl DMSO) is added to 5 mg of purified MAb in 5 ml PBS (pH 7.0) (13:1 molar ratio). After 4 h at 4° C., the mixture is extensively dialyzed in PBS.

0.5 mg rHV1 in 200 μl of acetate buffer (20 mM, pH 6.0) are mixed with 100 μg of biotin-X-N-hydroxysuccinimide ester (Calbiochem) dissolved in 40 μl ethanol/water (1:1, v/v) so that the molar ratio of biotin to rHV1 is 3.2:1, and the mixture is incubated 20 min at RT. Then, 260 μl of PBS are added and the solution is dialyzed overnight against PBS at 4° C.

5.2 Competitive ELISA

Epitope mapping is carried out by competitive ELISA experiments using rHV1, rHV1 analogues as described in example 4, and recombinant hirudin variant PA (rHV3; Dodt et al., Biol. Chem. Hoppe-Seyler 367, 803, 1983). The two-step competitive ELISA is performed as described in the following.

rHV1 (0.2 μg/100 μl 50 mM coating buffer) is absorbed onto microtiter plates. After overnight incubation at 4° C., the plates are washed with PBS-Tween 0.1%, and remaining free sites on the solid support are blocked by incubation with PBS/BSA (1% w/v). In separate test tubes, 50 μl of each purified MAb (40 to 400 ng/ml) are incubated with 650 μl of a standard solution containing increasing amounts of either rHV1 or rHV1 analogues. After overnight incubation at 4° C., 200 μl of the antibody-antigen mixture are added to each well and incubated for an additional hour. The wells are then washed five times, and 100 μl per well of goat anti-mouse antibody conjugated to alkaline phosphatase (dilution 1:1500) are added to the wells for 1.5 h. After washing, 150 μl per well of the substrate p-nitrophenylphosphate (1 mg/ml in diethanolamine buffer pH 9.8, supplemented with 0.5 mM $MgCl_2.H_2O$) are added to the wells. The change of colour, which is proportional to the amount of antibody reacting with the antigen bound to the solid phase, is monitored at 405 nm. All samples are run in triplicate.

Typical inhibition curves are obtained by plotting $B/Bo\times100$ (percent bound) vs. the concentration of inhibitor present (Bo represents absorbance measured without rHV1 added to the antibody, and B, absorbance measured with various concentrations of rHV1). The $IC_{50}$ value represents the concentration of antigen which inhibits 50% of the binding of the antibody to the solid phase. $IC_{50}$ is calculated using an adaption of the curve fitting programm ENZFITTER (R. J. Leatherbarrow, Elsevier) based on a four parameter logistic curve: $U=(D-C)/1+(z/A)b)+C$, where U is the expected response for a dose z of the standard. The four parameters describe the shape of the curve, D and C give the upper and lower asymptote, and A is the dose of the mid-asymptote (Raab, Clin. Chem. 29, 1757, 1983).

5.3 Double sandwich ELISA with MAbs selective for free hirudin to determine overlapping epitopes A double antibody sandwich ELISA using MAbs selective for free hirudin is carried out as described in the following to determine whether the monoclonal antibodies recognize overlapping epitopes.

Microtiter plates are coated with 0.5 μg/well of purified anti-THC MAb of group I prepared in sodium carbonate buffer (50 mM, pH 9.6), and incubated overnight at 4° C. After blocking and washing steps (by BSA 1% and PBS-Tween 0.1%, respectively), increasing concentrations of rHV1 prepared in PBS-Tween 0.1% (0 to 100 ng/well) are added to the bound MAb and incubated for 1 h at RT. After washing, a biotinylated second MAb selective for free rHV1 is added to the plate (0.5 μg/well) and incubated for 2 h. As second monoclonal antibody, MAb 4114-96-1, MAb 4120-37-7 and MAb 4049-83-12, respectively, as described by Schlaeppi et al. (loc. cit.) are employed. Then, after washing, 100 μl of alkaline phosphatase-conjugated streptavidin (diluted 1:2500) is added and incubated for 1.5 h at RT. After washing, the substrate (see example 5.2) is added and the absorbance is measured at 405 nm after different intervals of time, starting 15 min after the addition of the substrate.

5.4 Sandwich ELISA to determine the rHV1/thrombin-complex

The thrombin/rHV1-complex is prepared by mixing 3 pmol of α-thrombin (3000 NIH units/mg; CBR Laboratories) with 15 pmol of rHV1 in 100 μl PBS-Tween 0.1% containing 0.1% BSA or in 100 μl of human plasma diluted 1:3 in PBS-Tween.

Microtiter plates are coated with the anti-thrombin MAb EST6 (0.2 μg/100 μl; Bioscot, Edinburgh, UK). After overnight incubation at 4° C., blocking by PBS-BSA (0.1%) and washing with PBS-Tween, 100 μl of a series of two fold dilutions of the thrombin/rHV1-complex prepared as described above (1:5 molar ratio) are added to the well and incubated for 2 hours at room temperature. Then the following reagents are added consecutively: (1) 0.5 μg/100 μl biotinylated MAb 4107-76-1 and MAb 4158-81-7, respectively, for 2 h, (2) alkaline phosphatase-conjugated streptavidin (diluted 1:2500) for 1.5 h, (3) substrate (see example 5.2). The incubations are done at 22° C. Between each step, the plates are washed with PBS-Tween 0.1%. The absorbance is monitored at 405 nm after 15 to 30 min.

A simplified assay is developed using microtiter plates coated with the MAb of choice. Biotinylated thrombin (0.2 μg/well) complexed with rHV1 (molar ratio 1:1) is added to the wells, and the biotinylated thrombin is revealed directly by a alkaline phosphatase-conjugated streptavidin.

5.5 Gel filtration HPLC

Gel filtration HPLC (high pressure liquid chromatography) is used to analyze the thrombin/rHV1-complex or antibody-antigen complexes. Samples containing thrombin (0.3 nmol) and rHV1 (1.5 nmol) are incubated for 15 min. The tested anti-THC MAb or the control anti-hirudin MAb 4049-83-12 (0.2 nmol; Schlaeppi et al., loc. cit.) is added (total volume 45 μl) and further incubated for 5 h at room temperature. The samples are injected in a TSK-G3000SW gel filtration column (LKB; 8×300 mm) and eluted with PBS at a flow rate of 0.3 ml/min. The protein absorbance is monitored at 280 nm.

Example 6

Characterization of the monoclonal anti-THC antibodies 6.1 The monoclonal antibodies of group I The results of the competitive ELISA of example 5.2 for MAb 4158-81-7 (group I) are given in Table 1 below.

TABLE 1

Characterization MAb 4158-81-7 by competitive ELISA

| hirudin variant/analogue | $IC_{50}$ (ng/ml)[A] |
|---|---|
| rHV1 | 3.5 |
| rHV3[B] | 1000 |
| rHV1 1–43 | 1.0 |
| HV1 peptide 52–65 | >1000 |
| HV1 peptide 40–65 | >1000 |
| HV1 peptide 29–38 | >1000 |
| HV1 peptide 1–15 | >1000 |
| S-CM-rHV1[C] | 200 |
| rHV1 + V8 protease (2h)[D] | 0.5 |
| rHV1 + lysyl endopeptidase (1.5h)[E] | 11.8 |

Legend:
[A]inhibitor concentration for 50% inhibition of the solid phase MAb
[B]rHV3 residues which are different from rHV1: Ile 1, Thr 2, Lys 24, Gln 33, Lys 35, Asp 36, Gln 53, Pro 58, Asp 62, Ala 63, Asp 65, Glu 66
[C]reduced and S-carboxymethylated rHV1
[D]97% cleavage at Glu 43; 50% cleavage at Glu 61
[E]100% cleavage at Lys 47; 100% cleavage at Lys 36

MAb 4158-81-7 binds rHV1 in solution with an $IC_{50}$ value of 3.5 ng/ml but shows no crossreactivity with the four rHV1 peptides 1–15, 29–38, 40–65 and 52–65 which encompass most of the rHV1 sequence. In addition, the binding of reduced and S-carboxymethylated rHV1 is decreased drastically as compared to unmodified rHV1, suggesting a conformation dependent epitope. MAb 4158-81-7 completely crossreacts with the N-terminal core domain of rHV1, as well as with V8 protease-digested rHV1 in which the rHV1 core domain has remained intact. The affinity of the MAb for rHV1 1–43 and for V8-digested rHV1 is higher than for the whole rHV1 molecule, suggesting that some steric hindrance of the C-terminal domain occurs. Indeed, for immunization, rHV1 is linked to KLH mainly through its C-terminal domain, which might alter its native conformation.

In the double sandwich ELISA of example 5.3, MAb 4158-81-7 combines to any anti-hirudin MAb binding to the C-terminal domain (see Schlaeppi et al., loc. cit.), indicative of non-overlapping epitopes. However, ten- to twenty-fold higher concentrations of rHV1 are necessary when MAb 4158-81-7 is combined to MAb 4049-83-12 which binds to residues within the domain 41–47. This indicates a partial overlap between the epitopes of both MAbs which is further confirmed by limited proteolysis of the rHV1/antibody-complex by V8-protease. The cleavage between Glu 43 and Gly 44 is prevented by the binding of MAb 4158-81-7 to rHV1.

All the remaining MAbs of group I also crossreact with the rHV1 peptide 1–43, suggesting that the MAbs of group I bind only to the N-terminal core domain of rHV1. These results also indicate that the major antigenic determinants of rHV1 accessible on the surface of the thrombin/rHV1-complex are located exclusively in the N-terminal core domain, as suggested by the crystal structure of the thrombin/hirudin-complex (Grütter et al., EMBO Journal 9, 2361, 1990).

MAb 4158-81-7 does not bind to the thrombin/rHV1-complex in solution, but binds to the complex adsorbed on a solid surface such as a microtiter plate or presented by an antibody such as MAb EST6 or MAb 4107-76-1. In addition, MAb 4158-81-7 does not bind to the biotinylated thrombin/rHV1-complex (in contrast to MAb 4107-76-1, see below). Therefore, it is concluded that the conformation of the thrombin/rHV1-complex in solution is different from that on a solid support, and that the core domain of rHV1, to which MAb 4158-81-7 binds, becomes exposed only in the latter conformation. It follows that MAb 4158-81-7 crossreacts with the thrombin/rHV1-complex only under restricted conditions, but not in general.

6.2 The monoclonal antibodies of group II

Among the four MAbs of group II, only one MAb crossreacts with rHV1, however with low affinity. As shown by the competitive ELISA of example 5.2, this MAb also cross-reacts with the rHV1 core domain (residues 1–43), indicating that it is closely related to the MAbs of group I.

Among the remaining three MAbs, MAb 4107-76-1 is investigated in more detail since it binds very strongly to the thrombin/rHV1-complex. It neither binds to rHV1 nor to thrombin in solution. However, this MAb binds to thrombin adsorbed onto the microtiter plates. Several lines of evidence suggest that the binding occurs only when thrombin is absorbed onto a solid surface but not when it is in solution. Firstly, in gel filtration HPLC experiments as described in example 5.6, MAb 4107-76-1 binds to the complex, but not to free thrombin. The anti-rHV1 MAb 4049-83-12, which only recognizes free rHV1, is used as control. Secondly, using biotinylated thrombin, MAb 4107-76-1 binds only to the complex and not to free biotinylated thrombin, whereas the anti-thrombin MAb EST6 recognizes both. Finally, by double MAb sandwich ELISA using MAb EST6 to avoid a direct adsorption of thrombin onto the plate, the binding of MAb 4107-76-1 occurs only with the complex but not with free thrombin. When the rHV1 C-terminal peptide 40–65 replaces rHV1 in the complex, no binding of MAb 4107-76-1 occurs, suggesting that the whole rHV1 molecule is necessary for binding. However, replacing rHV1 by the variant rHV3 reduces the binding of MAb 4107-76-1 to the complex only partially, suggesting that the MAbs recognize a common determinant. Neither small molecular weight inhibitors nor heparin could induce binding of the MAb to thrombin. These results suggest that MAb 4107-76-1 recognizes a neoepitope on thrombin expressed either upon binding of rHV1 or upon adsorption of thrombin onto a solid surface. Thrombin undergoes a conformational change upon binding of rHV1 (S. Konno et al., Arch. Biochem. Biophys. 267, 158, 1988), as confirmed by crystallographic data (Grütter et al., loc. cit.). This conformational change might create immunodominant neoepitopes. Conformational change or even partial denaturation of an antigen upon adsorption on a solid surface is well documented and could explain the binding of MAb 4107-76-1 to surface-adsorbed thrombin.

Some test results for the group II monoclonal antibody MAb 4107-76-1 are given in Table 2.

TABLE 2

ELISA determination of the binding of the thrombin/rHV1-complex to the MAbs

| reagents added[A] | absorbance (405 nm) MAb 4107-76-1 | MAb EST 6 |
|---|---|---|
| biotinylated thrombin | 0.040 | 0.719 |
| biotinylated thrombin and rHV1 | 1.027 | 1.018 |
| biotinylated rHV1 | 0.013 | 0.020 |
| PBS-Tween | 0.009 | 0.017 |

[A] The reagents are added to microtiter plates coated with MAbs and are revealed by alkaline phosphatase-conjugated streptavidin Example 7

Sandwich ELISA for determination of the thrombin/hirudin-complex in plasma

The specific determination of the thrombin/hirudin-complex in plasma is achieved by the sandwich ELISA using MAb 4107-76-1 as capture antibody and biotinylated MAb 4158-81-7 as second antibody. The ELISA is a modification of the ELISA described in example 5.4 by replacing MAb EST6 with MAb 4107-76-1, and is carried out as described in the following.

Microtiter plates are coated with MAb 4107-76-1 (0.2 μg/100 μl). After blocking by PBS-BSA 1% and washing with PBS-Tween 0.1%, 200 μl of plasma to be tested are added to the well and incubated for 2 h. Then the following reagents are added consecutively: (1) 0.5 μg/100 μl biotinylated MAb 4158-81-7 for 2 h, (2) alkaline-phosphatase-conjugated streptavidin (diluted 1:2500) for 1.5 h, (3) substrate (see example 5.2). The incubations are done at 22° C. Between each step, the plates are washed with PBS-Tween 0.1%. The absorbance is monitored at 405 nm after 15 to 30 min.

The test allows the determination of the presence and/or the concentration of the thrombin/hirudin-complex in concentrations ranging from 1 to 200 ng/ml.

Example 8

Test kit for an ELISA for determination of the thrombin/hirudin-complex

A test kit for the ELISA described in example 7 contains:

polyvinyl chloride microtiter plates;
20 ml of monoclonal antibody MAb 4107-76-1 (10 μg/ml) in coating buffer;
20 ml of biotinylated MAb 4158-81-7 in PBS-Tween 0.1% (5 μg/ml);
2 ml standard solution containing 5 μg rHV1;
300 ml of PBS-Tween 0.1%;
300 ml of PBS-BSA 1%;
0.5 ml of alkaline phosphatase-conjugated streptavidin;
50 ml of p-nitrophenyl phosphate (1 mg/ml) in diethanolamine buffer (10%, 0.5 mM $MgCl_2$, 0.02% $NaN_3$, adjusted to pH 8.9 with HCl);
calibration curve;
colour intensity scale;
instruction manual.

I claim:

1. A monoclonal antibody which is directed against the thrombin/hirudin-complex, or a derivative thereof which retains the specificity of said antibody.

2. A monoclonal antibody according to claim 1, wherein the hirudin is hirudin variant 1.

3. A monoclonal antibody according to claim 1, wherein the hirudin is recombinant hirudin.

4. A monoclonal antibody according to claim 1, wherein the hirudin is recombinant hirudin variant 1.

5. A monoclonal antibody according to claim 1, which recognizes determinants of the hirudin moiety in the thrombin/hirudin-complex.

6. A monoclonal antibody according to claim 4, which recognizes determinants of the recombinant hirudin variant 1 moiety.

7. A monoclonal antibody according to claim 6, which recognizes determinants within the N-terminal core domain of the recombinant hirudin variant 1 moiety.

8. The monoclonal antibody according to claim 6, designated MAb 4158-81-7.

9. A monoclonal antibody according to claim 1, which recognizes determinants of the thrombin moiety.

10. A monoclonal antibody according to claim 4, which recognizes determinants of the thrombin moiety.

11. A monoclonal antibody according to claim 10, which recognizes determinants of the thrombin moiety which becomes exposed for antibody binding only when thrombin is bound to hirudin or to a solid surface, but which does not bind to free thrombin in solution.

12. The monoclonal antibody according to claim 10, designated MAb 4107-76-1.

13. A derivative of a monoclonal antibody according to claim 1, which is a conjugate of said antibody and an enzyme, a fluorescent marker, a chemiluminescent marker, a metal chelate, avidin, biotin or paramagnetic particles.

14. A derivative of a monoclonal antibody according to claim 1, which is radioactively labelled.

15. A derivative of a monoclonal antibody according to claim 1, which is a fragment.

16. A process for the preparation of a monoclonal antibody or a derivative thereof according to claim 1, comprising the steps of:
  culturing hybridoma cells capable of producing the monoclonal antibody in vivo or in vitro under conditions suitable for the production of the monoclonal antibody by the hybridoma cells; and
  isolating the thus-produced monoclonal antibody therefrom.

17. A hybridoma cell line capable of producing a monoclonal antibody according to claim 1.

18. A hybridoma cell line according to claim 17, which is a hybrid of myeloma cells and B lymphocytes isolated from a mammal immunized with hirudin coupled to a suitable carrier or with the thrombin/hirudin complex.

19. A hybridoma cell line according to claim 18, which is a hybrid of mouse myeloma cells and B lymphocytes isolated from a mouse immunized with recombinant hirudin variant 1 (rHV1) coupled to a suitable carrier or a thrombin/rHV1 complex.

20. The hybridoma cell line according to claim 17, designated 4158-81-7 which was deposited at the European Collection of Animal Cell Cultures (ECACC) under the number 90061405 on Jun. 14, 1990.

21. The hybridoma cell line according to claim 17, designated 4107-76-1 which was deposited at the European Collection of Animal Cell Cultures (ECACC) under the number 90061404 on Jun. 14, 1990.

22. A process for the preparation of a hybridoma cell line according to claim 17, comprising the steps of:
  immunizing an animal with a hirudin-carrier conjugate or a thrombin/hirudin-complex;
  isolating antibody-producing cells from the thus-immunized animal;

fusing the antibody-producing cells with cells of a continuous cell line whereby hybrid cells having the replicative abilities of the continuous cell line are produced;

cloning the hybrid cells; and isolating the clones capable of producing the monoclonal antibodies.

23. A method for the qualitative or quantitative determination of the thrombin/hirudin-complex in a fluid suspected of containing the complex, comprising contacting the fluid with a monoclonal antibody of claim 1.

24. A test kit for the qualitative or quantitative determination of the thrombin/hirudin-complex, comprising a monoclonal antibody according to claim 1.

25. A method of claim 23, wherein the fluid is a buffer, urine or plasma.

* * * * *